Oct. 15, 1940. S. HAHN Plant Pat. 430
IVY PLANT
Filed Feb. 12, 1940
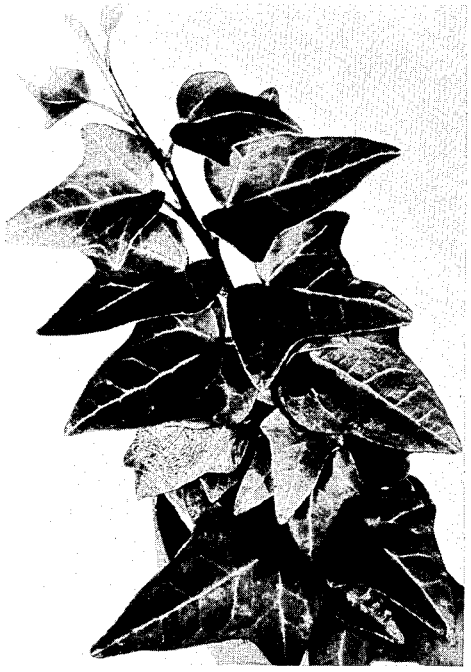
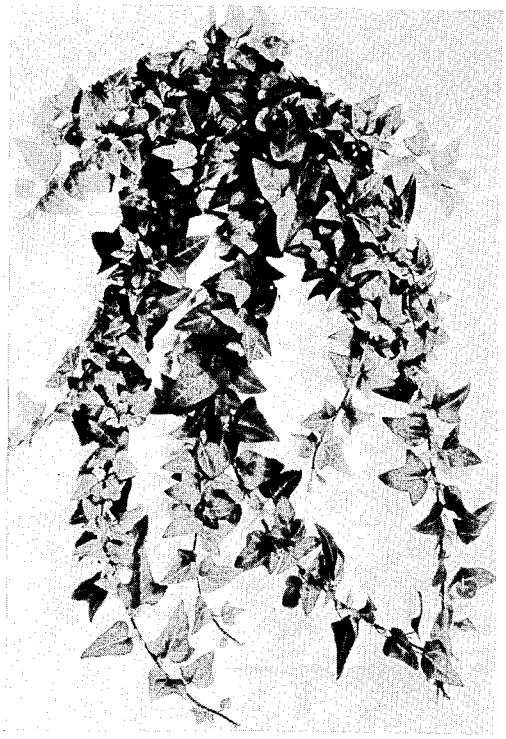
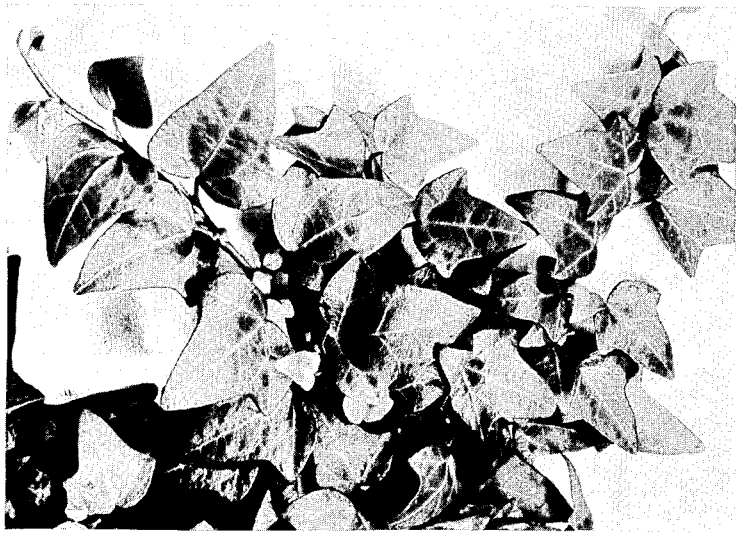
INVENTOR
Sylvan Hahn
By Orville M. Kile
Plant Patent Agent Patented Oct. 15, 1940

Plant Pat. 430

UNITED STATES PATENT OFFICE

430

IVY PLANT

Sylvan Hahn, Pittsburgh, Pa.

Application February 12, 1940, Serial No. 318,577

1 Claim. (Cl. 47—59)

My new variety was discovered by me as a sporting branch growing from a plant of the variety Hahn's Self-branching Ivy and has been reproduced by means of cuttings for several years.

The accompanying illustration shows a month-old specimen of this variety in a pot, a three-month specimen in which the self-branching habit is very noticeable and a third plant which is about five months old and shows the pendulous habit of this variety which prevails after it has reached the height of eight or ten inches.

The most outstanding characteristic of this new variety is its compactness of growth, its natural growth being much more compact and dense than that of any other known ivy of the large-leaf class.

The variety is a very rapid grower and is freely self-branching. Without trimming or cutting it produces a large number of side shoots or branches and this tends to make a dense growth. The variety is able to produce salable plants in a much shorter time than any other varieties of ivy now on the market.

Most of the leaves of this variety are somewhat hastate in shape, with three lobes—a long center lobe sloping down to the side lobes with a very slight indentation, and with a rounded base. However, sometimes the variety has some leaves that are somewhat heartshaped and without lobes or indentations. The leaves vary in size according to growing conditions. The usual size is 2¼ to 2½ inches in length by 1¾ to 2¼ inches in width from lobe to lobe. The color of the leaves is ordinarily darker than most ivy varieties but varies according to the stage of growth or the kind and quantity of plant food used. The surface of the leaves is somewhat waxy and their veining is prominent. The matured leaves are leathery and of excellent substance.

The nodes are very short, allowing the leaves to be set close together on the stems and to overlap one another. Because of the short petioles or leaf stems, the leaves are set close to the main stem. Both of these features increase the compactness of growth of the variety.

This variety has an upright habit of growth until it has attained a height of four or five inches, then it develops a pendulous habit of growth and can be grown to an indefinite length.

Having thus disclosed my discovery, I claim:

A new and distinct variety of ivy plant characterized particularly by its intense compactness and density of growth; its close-set, overlapping leaves of distinctive shape as described; its habit of growing first upright and later pendulous; and its rapidity of growth and freedom of self-branching which enable it to produce salable plants in an unusually short time.

SYLVAN HAHN.